US010966830B2

(12) United States Patent
Schaffner et al.

(10) Patent No.: US 10,966,830 B2
(45) Date of Patent: Apr. 6, 2021

(54) MEDICAL APPARATUS AND METHOD FOR HEART VALVE REPAIR

(71) Applicant: CoreMedic AG, Biel (CH)

(72) Inventors: Silvio Schaffner, Berlingen (CH); Tobias Aeschlimann, Burgdorf (CH); Oliver Wüthrich, Herrenschwanden (CH); Thomas Bauer, Allensbach (DE)

(73) Assignee: COREMEDIC AG, Biel (CH)

( * ) Notice: Subject to any disclaimer, the term of this patent is extended or adjusted under 35 U.S.C. 154(b) by 183 days.

(21) Appl. No.: 15/768,884

(22) PCT Filed: Oct. 19, 2016

(86) PCT No.: PCT/CH2016/000137
§ 371 (c)(1),
(2) Date: Apr. 17, 2018

(87) PCT Pub. No.: WO2017/066889
PCT Pub. Date: Apr. 27, 2017

(65) Prior Publication Data
US 2019/0175346 A1    Jun. 13, 2019

(30) Foreign Application Priority Data
Oct. 21, 2015 (CH) .................... 1534/15

(51) Int. Cl.
*A61F 2/24* (2006.01)
*A61B 17/04* (2006.01)
*A61B 17/00* (2006.01)

(52) U.S. Cl.
CPC ........ *A61F 2/2457* (2013.01); *A61B 17/0401* (2013.01); *A61F 2/2466* (2013.01);
(Continued)

(58) Field of Classification Search
CPC .................... A61F 2/2457; A61F 2/2466
See application file for complete search history.

(56) References Cited

U.S. PATENT DOCUMENTS

| 2011/0011917 A1 | 1/2011 | Loulmet |
| 2011/0029071 A1* | 2/2011 | Zlotnick .......... A61B 17/00234 623/2.11 |

(Continued)

FOREIGN PATENT DOCUMENTS

| EP | 2 410 948 | 2/2012 |
| WO | 2012/040865 | 4/2012 |

OTHER PUBLICATIONS

International Preliminary Report on Patentability dated Apr. 24, 2018 (dated Apr. 24, 2018), Application No. PCT/CH2016/000137, 8 pages.

*Primary Examiner* — Suba Ganesan
(74) *Attorney, Agent, or Firm* — Rankin, Hill & Clark LLP

(57) ABSTRACT

An instrument for repairing an atrioventricular heart valve, the instrument including a tubular element having an outer, distal end; a distal implant part arranged in the tubular element; an artificial chord arranged in the tubular element; a proximal implant part arranged in the tubular element; and, an anchor carrier arranged in the tubular element. The distal implant part and the proximal implant part are arranged in the tubular element beside one another, with the distal implant part being closer to the distal end of the tubular element than the proximal implant part The proximal implant part is assembled with the anchor carrier inside the tubular element so that the tubular element prevents the proximal implant part from escaping from the anchor carrier as long as the anchor carrier is within the tubular element.

17 Claims, 4 Drawing Sheets

(52) U.S. Cl.
CPC ............ *A61B 2017/00243* (2013.01); *A61B 2017/0406* (2013.01); *A61B 2017/0409* (2013.01); *A61B 2017/0417* (2013.01); *A61B 2017/0437* (2013.01); *A61B 2017/0458* (2013.01); *A61B 2017/0464* (2013.01)

(56) References Cited

U.S. PATENT DOCUMENTS

| | | |
|---|---|---|
| 2012/0226294 A1 | 9/2012 | Tuval |
| 2015/0142101 A1 | 5/2015 | Coleman et al. |
| 2015/0250590 A1* | 9/2015 | Gries ................ A61B 17/0401 623/2.11 |
| 2017/0252032 A1* | 9/2017 | Hiorth ................ A61F 2/2466 |

* cited by examiner

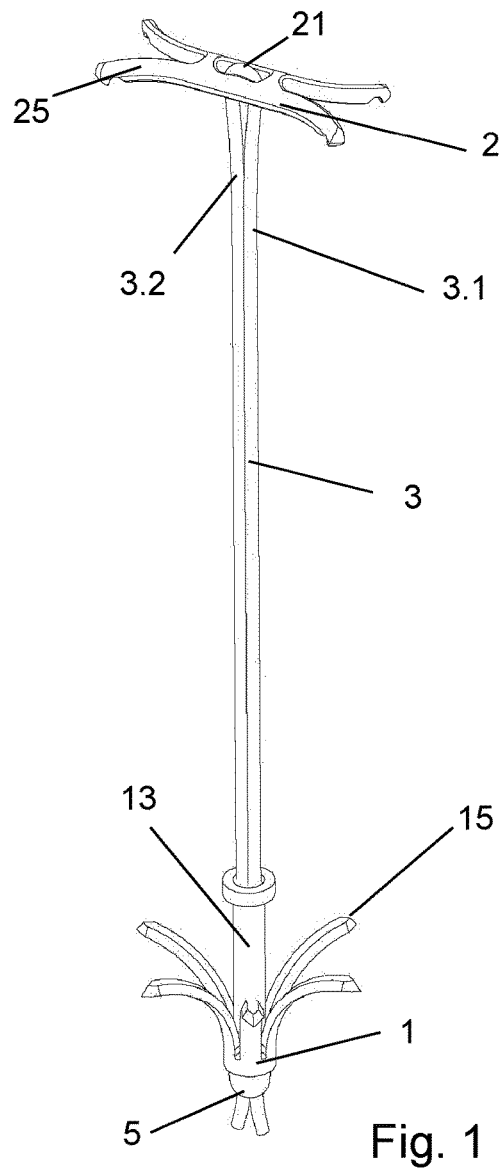
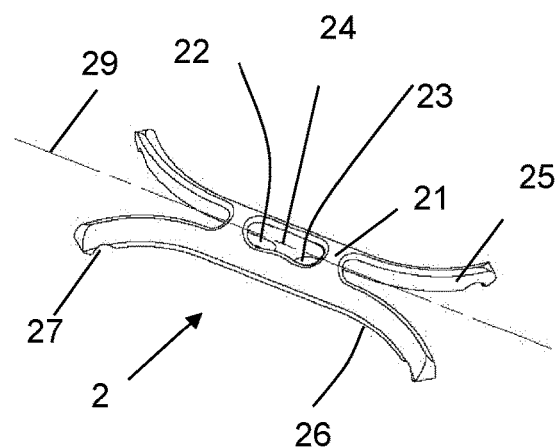
Fig. 2
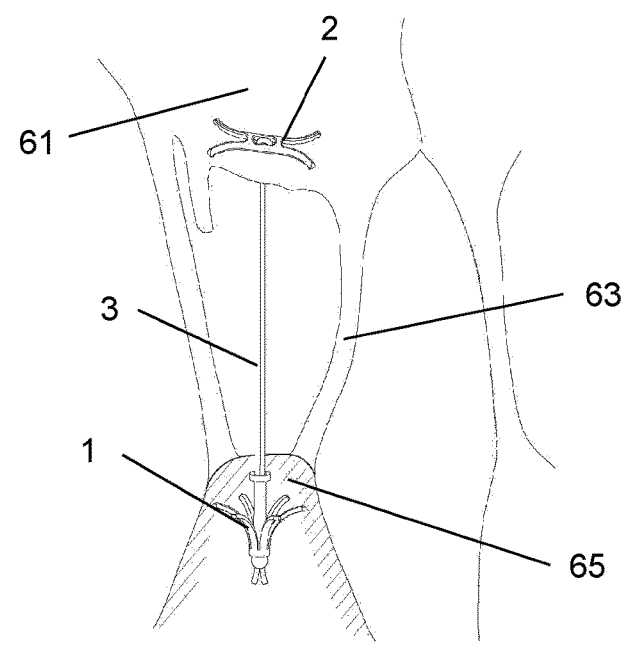
Fig. 1
Fig. 3

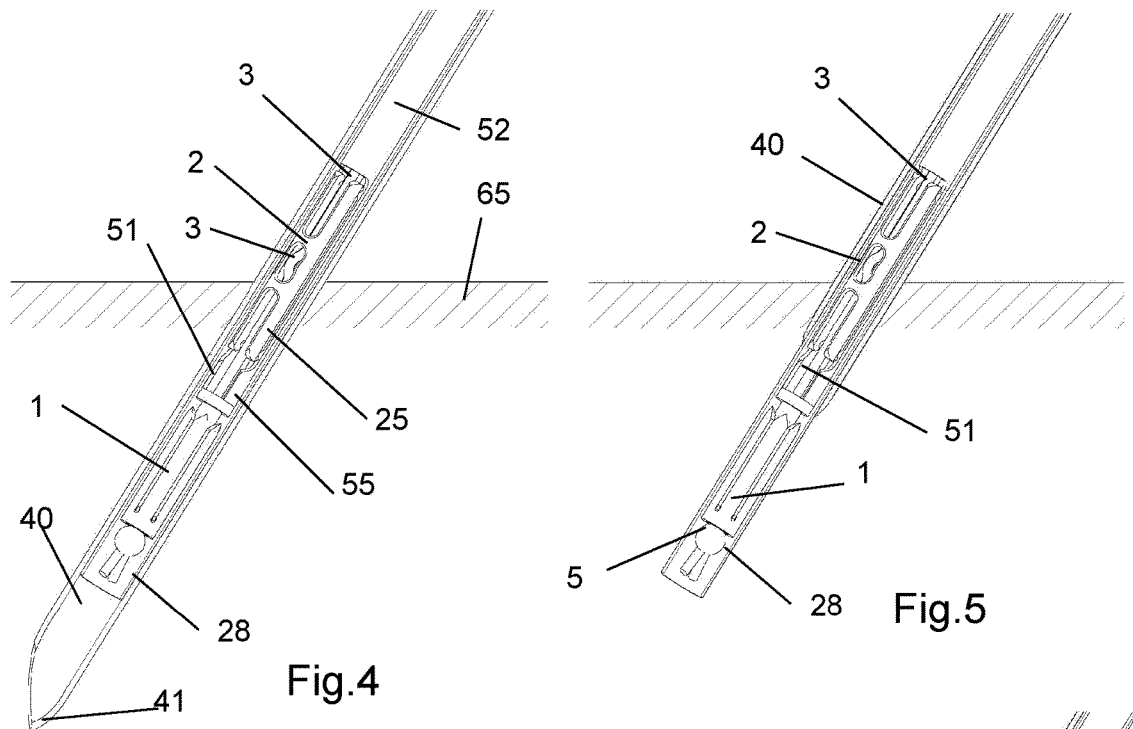
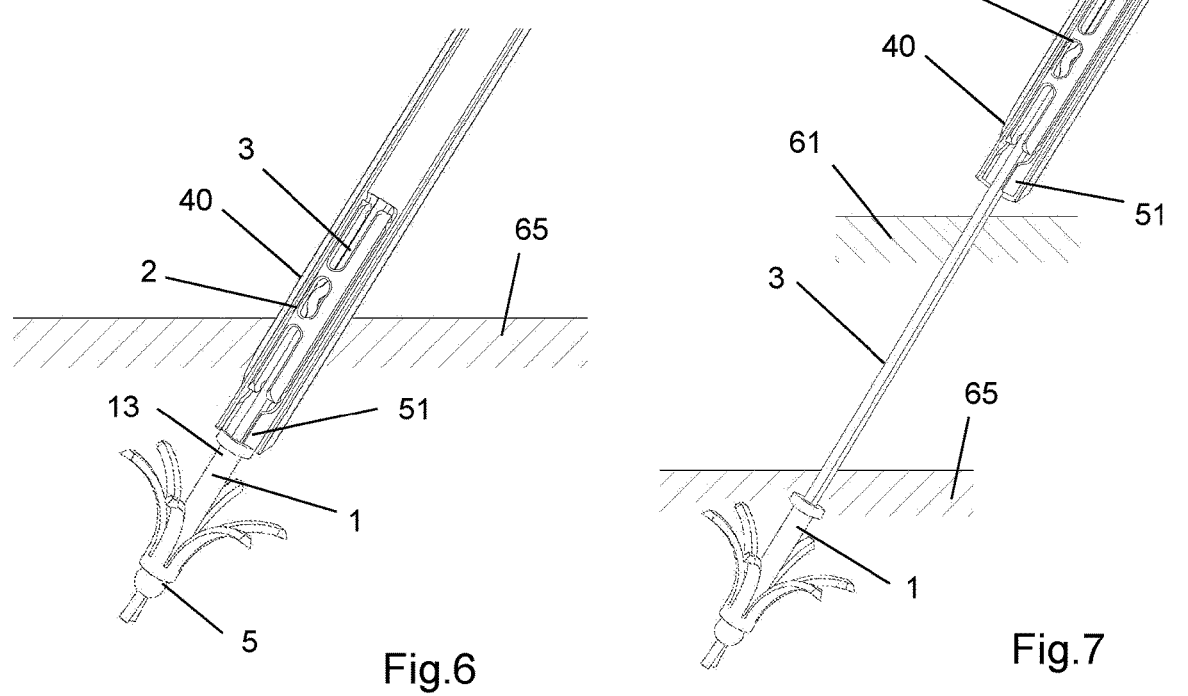

MEDICAL APPARATUS AND METHOD FOR HEART VALVE REPAIR

BACKGROUND OF THE INVENTION

Field of the Invention

The invention is in the field of surgical, for example minimally invasive (especially interventional radiology), devices for heart valve repair. It more particularly relates to a system for repairing an atrioventricular heart valve, in particular the mitral heart valve or also the tricuspid heart valve, in a minimally invasive manner, and to an according method or implanting an implant.

Description of Related Art

Prolapses of a leaflet of the mitral valve into the left atrium and resulting valve insufficiency can cause serious dysfunctions of the heart. One reason for such prolapse is a damaging of the tendons (chordae tendineae) that connect the leaflets of the mitral valve to the papillary muscle through the left ventricle. Such damage may, for example, be a result of a myocardial infarction.

A repair of such a prolapse demands the leaflet or leaflets to be re-connected to the papillary muscle, for example by synthetic fibres, such as Gore-Tex® fibres. Such an approach in accordance with the state of the art demands suturing the implant to a papillary muscle. A first disadvantage of such a repair process is that it is only possible while the heart is inactive, thus the surgical repair demands that the heart is stopped and drained of blood, while a cardiopulmonary bypass is used. A second disadvantage is that the success of the operation depends strongly on the skill of the surgeon. A further disadvantage is that the fibres sutured to the leaflet may cause long-time damage.

In WO 2012/040865, approaches are presented according to which a distal anchor attached to a filament serving as artificial chord is used that can be shot across the left ventricle. Also tools for fixing an artificial chord to the leaflet and tools for temporary fixation of the leaflet of the beating heart are illustrated.

US 2011/0011917 describes methods and devices for cardiac valve repair. The devices may include a dart anchor with self-expandable legs for being secured into cardiac tissue and a staple to be deployed into tissue of the leaflet, which staple may be secured to a tensile member that is also connected to the dart anchor. A pledget may be used to spread loads, i.e. to prevent the leaflet tissue from being injured by the staple. US 2011/0011917 also discloses an anchor with an eyelet in which a chord can slide. This anchor is to be attached to a leaflet.

SUMMARY OF THE INVENTION

It is an object of the present invention to provide an instrument for repairing an atrioventricular heart valve, in particular the mitral heart valve or also the tricuspid heart valve, and an according method, which instrument and method overcome drawbacks of prior art devices and methods and which ensure easy implantation, are suited also for interventional surgery and provide a reliable and well tissue-compliant repair.

According to an aspect of the invention, a system (arrangement) for repairing an atrioventricular heart valve is provided, the system including:
a tubular element having an outer, distal end,
a distal implant part arranged in the tubular element,
an artificial (or possibly allograft or xenograft) chord arranged in the tubular element,
a proximal implant part arranged in the tubular element, and
an anchor carrier arranged in the tubular element,
the distal implant part and the proximal implant part being arranged in the tubular element beside one another, for example with the distal implant part being closer to the distal end of the tubular element than the proximal implant part,
the proximal implant part being assembled with the anchor carrier inside the tubular element so that the tubular element prevents the proximal implant part from escaping from the anchor carrier as long as the anchor carrier is within the tubular element.

Especially, the proximal implant part may be assembled with the anchor carrier in a manner that it can escape and is released automatically as soon as the proximal implant part and the portion of the anchor carrier to which it is mounted is outside of the tubular element—for example without any active mechanism that causes the release, thus just by being moved out of the tubular element.

For example, the anchor carrier may axially extend within the tubular element from proximally of the proximal implant part to at least a center of the proximal implant part and, for example, at least to its distal end or further than its distal end. Especially, the anchor carrier may extend over the full (proximodistal) length of the proximal implant part.

In embodiments, the anchor carrier may form a seat for the proximal implant part, out of which the proximal implant part can escape by being moved in radial direction once it is released from the tubular element, i.e. the seat is open towards one radial direction but blocks the second implant part with respect to axial directions as long as it is kept in the seat by the tubular element.

The seat for this purpose may have a structure adapted to the shape of the proximal implant part in the initial (not spread) state. Especially, the anchor carrier may have a distal foot portion with a channel for the chord, and, proximally thereof, a seat portion (also referred to as shaft portion in this text) in which the cross section is reduced to accommodate the proximal implant part. Proximally of the seat portion, the anchor carrier may have a pusher portion that has a larger cross section than the seat portion so that a pushing movement of the anchor carrier also pushes the second implant part forward as long as the second implant part is still located in the seat and not yet released.

The anchor carrier at least in a distal region including the foot portion and the seat portion may be formed of a tube, with the channel for the chord and the seat being formed by recesses in the tube.

The anchor carrier may include a stop feature cooperating with the proximal implant part to secure the same against movements into distal directions relative to the anchor carrier as long as the proximal implant part is within the tubular element.

The anchor carrier may especially include a shaft portion extending along the proximal implant part and a foot piece distally of the shaft portion, the foot piece forming a proximally-facing shoulder forms the stop feature and secures the proximal implant part against being pulled out into distal directions. Especially, a distal end of the proximal implant part or another portion of the proximal implant part may lie against the shoulder in the assembled state of the system. The construction with a foot piece may especially be useful after the distal implant part has been released and implanted in muscle tissue, when it cannot be ruled out that the chord couples such pulling forces into the proximal implant portion, especially when the operation is carried out in the beating heart, or also due to friction arising if the chord is being pulled upon retreatment of the tubular element from the site where the distal implant part is implanted.

The foot piece may be open towards one side (with respect to radial directions) so that the chord in the assembled state can be guided through the foot piece but is prevented being entrapped in the anchor carrier after release of the proximal implant part. Thus, the foot piece may form a channel open towards one lateral side for the chord. Alternatively, it would also be possible to provide the foot piece in a manner that it does not engage a full cross section of the tubular element, with the chord running next to the foot piece.

The fact that the proximal implant part and the distal implant part are arranged beside each other means that these implant parts are not for example, mounted one inside the other. Rather, they are next to each other; this does not rule out that they have portions the axial position of which overlap or that there is a part of another item between them so that they are at a distance from each other.

Due to this construction, the implant parts can be implanted as follows:

The tubular element may be a tube with a piercing distal end, i.e. it may be or include a cannulated needle. Alternatively, the tubular element may be a sleeve without any capability of piercing. In the latter case, the system may further include a tube with a piercing distal end (cannulated needle) encompassing the sleeve. Then, the sleeve may protect the chord and/or other implant parts from the sharp distal end of the tubular element.

In a first step, the tubular element is guided through a perforation of a leaflet of the valve to be repaired. As mentioned example, the tubular element to this end may have a distal piercing tip so as to be a needle, or it may be arranged inside a cannulated needle. Then, in a second step, the tubular element is guided to a tissue portion—for example the papillary muscle—of the heart in which the distal implant part is to be anchored. For example, the tubular element may be inserted into the tissue so as to be brought in a position in which the distal implant part inside the tubular element is fully within the tissue and can be anchored in the tissue by releasing the tubular element while keeping the distal implant part position constant. Then, the distal implant part is released into the tissue to be anchored therein. To this end, the distal implant part, and for example both implant parts and the anchor carrier is/are moved relative to the tubular element in a distal direction until the distal implant part is released. Radially spreading features of the distal implant part, such as self-extending barbs or the like, may then deploy and assist the anchoring in the tissue. In a further step, the tubular element is retracted to the perforation of the leaflet. Then, the proximal implant part and the anchor carrier are again moved to the distal direction relative to the tubular element, for example again by retracting the tubular element while holding the proximal implant part still. This releases the proximal implant part. Especially, the proximal implant part may be mounted to the anchor carrier in a manner that, if inside the tubular element, the proximal implant part is fixed relative to the anchor carrier, but absent the tubular element it is free to move relative to it.

After the proximal implant part has been released, it will automatically undergo a twisting movement relative to the tubular element axis and be oriented relative to the leaflet tissue, for example so that an abutment surface can rest against the tissue.

The chord will, after implantation, be mechanically coupled to both, the proximal implant part and the distal implant part. In a group of examples, the chord is pre-mounted to the proximal and distal implant parts so that their relative distance is pre-set.

The chord may connect the proximal and distal implant parts, especially by being secured to both of them. The chord in this may be fixedly fastened or slidingly secured.

In embodiments, the chord may run through the proximal implant part from a distal side to a proximal side thereof. The chord may especially be oriented backward in the tubular element, i.e. it may be arranged proximally of the proximal implant part. This means that any excess length portions that result from the distal and proximal implant parts being arranged next to each other are taken back to proximally of the proximal implant part (of course, this does not exclude that an end or both ends of the chord run over the proximal implant part to the distal implant part to which it is/they are secured).

in a first group of embodiments, the chord is taken doubly, by running from the distal implant part through a first opening of the proximal implant part, being looped back through a second opening of the proximal implant part and running back to the distal implant part, wherein the chord for example is displaceable with respect to the proximal implant part.
   In a second group of such embodiments, the chord has a stop feature, such as a knot, proximally of the proximal implant part. In the assembled state prior to the implantation, the knot is at a distance from the proximal implant part, proximally thereof.

The chord may have a fixed, pre-defined length that pre-defines the maximum distance of the proximal and distal implant parts after implantation. To this end, in the above-mentioned first group of embodiments, both ends of the chord may be secured to the distal implant part, for example by being crimped, secured by an adhesive or weld etc. or by being guided through a cannulated axial shaft and provided with a knot each distally of the shaft. The chord is then looped through the proximal implant part, for example by running through two openings from the distal to the proximal side and back to the distal side. In the mentioned second group of embodiments, the chord is secured to the distal implant part (again by being crimped or otherwise fixedly fastened or by a knot) and has a pre-made knot at the proximal end. Also other embodiments are possible, for example with a plurality of chords or with the chord being looped through the proximal implant part but not slidingly, etc.

In an alternative group of embodiments, the chord length may be determined and fixed by the surgeon in situ, for example by a crimp or a knot. The system then includes the chord with excess length.

In embodiments, the chord is coupled to the proximal implant part in a manner that a pulling force on the chord does not transmit any torque on the proximal implant part lying flat on the leaflet.

In embodiments with a single chord portion running between the proximal and distal implant parts, this may be achieved by placing the location of attachment of the chord in a center of area of with respect to the abutment surface.
   In embodiments with a plurality of chord portions running between the proximal and distal implant parts, this may be achieved by placing the center between the locations of attachment of the chord (for example the through openings through which the chord runs) at the location of the center of area with respect to the abutment surface.

The proximal implant part in contrast to prior art approaches may be configured to lie flat on a surface of the leaflet tissue, with the chord extending from the proximal implant part through the leaflet tissue and through the ventricle to the distal implant part. To this end, the proximal implant part may, for example, include a flattish distally-facing abutment surface (distally-facing in the implanted state, i.e. facing to the side to which the chord runs). This is in contrast to prior art approaches that teach to clamp the leaflet by a leaflet anchor or to other prior art approaches that teach to suture the leaflet.

Especially, the proximal implant part may be configured to only lie on the leaflet and to thereby being secured to it—without the proximal implant part having any fastening mechanism that extends within the leaflet or through the leaflet.

The proximal implant part may hold to the leaflet without any additional fastening mechanism (such as a suture) or artificial fastening means, only by the design of the implant as such that includes the distally facing abutment surface lying on the leaflet tissue—especially by the chord extending through the leaflet tissue and the ventricle to the distal implant part, possibly assisted by a distally-facing structure on the abutment surface that includes portions that protrude into the tissue, without penetrating through it, and/or is indented with respect to it, to prevent shifting movements.

The proximal implant part especially will, after implantation, be placed on one side of the leaflet only and not for example extend through the leaflet. The side on which the proximal implant part lies on the leaflet tissue is the atrium-facing upper side of the leaflet.

Especially, the proximal implant part is free of any clamping mechanism and does not include any portion that bears against the ventricle-facing lower surface of the leaflet.

As such, the proximal implant part is capable of coupling distally facing forces (forces towards the side of the ventricle) into the leaflet but its structure would not allow to couple proximally-facing forces into the leaflet (the proximal implant part cannot pull the leaflet towards the atrium side) and vice versa.

The method includes the steps of providing a system for replacing or supplementing damaged natural chordae tendineae of a human or animal heart, especially of the above-described kind, and further comprises:
  advancing the tubular element from an atrial side to a leaflet of an atrioventricular valve of the heart, piercing the leaflet and advancing the tubular element through the thus generated piercing hole of the leaflet and through the ventricle towards tissue of the heart, especially muscle tissue;
  releasing the distal implant part from the tubular element and thereby implanting it in the muscle tissue;
  retracting the tubular element and releasing the proximal implant part proximally of the leaflet, on the atrial side thereof; and
  removing the tubular element,
  wherein either the proximal implant part and the distal implant part are connected by the chord in the system, or the method includes the additional step of connecting the proximal and distal implant parts by the chord.

In contrast to prior art approaches, therefore, one instrument (the tubular element) is used for dispensing both, the distal and the proximal implant part, at two different locations in the heart.

Also in contrast to prior art approaches, the instrument that is used to release the distal implant part runs through the leaflet.

Releasing the proximal implant part may include advancing the anchor carrier relative to the tubular element in a distal direction until the proximal implant part is outside of the tubular element, whereby the proximal implant part is released automatically from the anchor carrier. Optionally, releasing the proximal implant part may then include letting a self-expanding portion of the proximal implant part expand. The expansion of the self-expanding portion (such as an arm of the proximal implant part) may assist release from the anchor carrier.

BRIEF DESCRIPTION OF THE DRAWINGS

Hereinafter, principles and embodiments of the invention are described referring to drawings. In the drawings, same reference numbers refer to same or analogous elements. The drawings show:
FIG. 1 an implant having a proximal implant part and a distal implant part, coupled by a chord;
FIG. 2 the proximal implant part;
FIG. 3 the implant implanted in a human heart;
FIG. 4 a system including the implant as well as a tube, a sleeve and an anchor carrier;
and
  FIGS. 5-9 the system of FIG. 4 during subsequent implantation steps.

DESCRIPTION OF THE PREFERRED EMBODIMENTS

Figure 8:
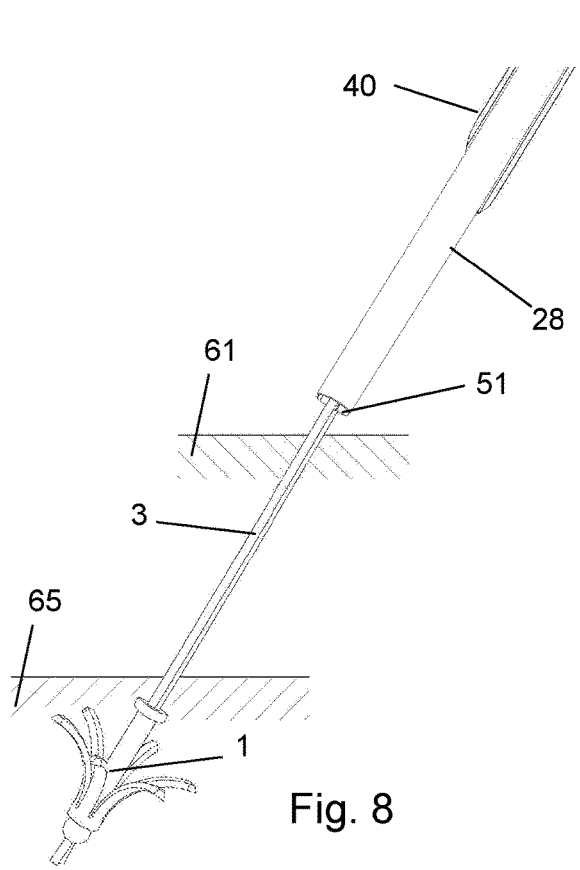

The implant illustrated in FIG. 1 includes a distal implant part 1, a proximal implant part 2 and a chord 3 connecting the proximal and distal implant parts. The chord is guided from a distal end of the distal implant part to the proximal implant part and through the proximal implant part back to the distal end of the distal implant part, so that the chord 3 is doubled and has two chord portions 3.1, 3.2 between the proximal and distal implant parts. Within the distal implant part and between the distal and proximal ends thereof, the chord portions 3.1, 3.2 are guided in a shaft 13, and they are secured by a knot 5 distally of the distal implant part.

In alternative embodiments, instead of a knot, other techniques could be used for securing the distal implant part to the chord, for example crimping, welding, etc.

The distal implant part 1 includes the shaft 13 having a longitudinal through opening for the chord and a plurality of legs 15 protruding backwardly and being bent radially outwardly.

The proximal implant part 2 is shown in somewhat more detail in FIG. 2. The proximal implant part is elongate defining a longitudinal axis 29. It has a central body 21 and four arms 25 one-piece with the central body and extending outwardly from the central body.

The lower side of the central body and the arms forms an abutment surface that after implantation rests against the leaflet tissue after implantation.

The chord 3 mechanically couples the proximal implant part 2 and the distal anchor part 1 with each other and defines a maximum distance between these implant parts. To this end, the proximal implant part has a first chord opening 22 and a second chord opening 23 separated by a bridge 24. The chord runs through the first chord opening, over the bridge and back to the second chord opening so that it is looped through the proximal implant part. The bridge 24 has rounded features so that the chord can slide along it easily without being damaged. The first and second openings are positioned so that the center of the abutment area is in the middle between them.

Because the openings are centrally located in the proximal implant part, a pulling force coupled into the chord acting on the proximal implant part will not cause any torque on the proximal implant part.

While in the depicted configuration the chord 3 is doubled and looped through the proximal implant part, this effect could, for example, also be achieved if the chord was one-way only and attached to a spot of the center of area or runs through a single opening in the center of area.

The arms 25 of the proximal implant part 2 are bent outwardly away from the axis. Thereby, the proximal implant part is better supported by the leaflet tissue. On the abutment surface, the arms each include an optional hook feature 27.

In embodiments, the central body may further include optional shallow lateral recesses [not shown] close to the transition to the arms 25 that cause a waist. This makes the proximal implant part more flexible to the outward bending of the arms.

FIG. 3 shows the distal implant part 1 anchored in the papillary muscle. The artificial chord 3 runs through the ventricle and through an opening of the leaflet; the proximal implant part is placed on the proximal side of the leaflet 61, with the abutment surface resting on the leaflet tissue. By this, the implant assists the natural chordae 63 if they are damaged or otherwise not sufficient for the mitral valve to close sufficiently.

In FIG. 4 the system is shown in the assembled state, and FIGS. 5-9 show the system of FIG. 4 during subsequent implantation steps. The distal implant part 1 and the proximal implant part 2 are both arranged inside a sleeve 28 that is guided inside a tube 40. In the figures (with the exception of FIGS. 8 and 9), the sleeve 28 and the tube 40 are shown transparent so that the elements inside are visible. The tube has an inner diameter of about 1.2 mm and an outer diameter of 1.5 mm.

The sleeve 28 in addition to the distal and proximal implant parts also contains the chord 3 that runs from the distal implant part 1 through the openings 22, 23 and forms a loop proximally of the proximal implant part.

Further, the system includes an anchor carrier 51. The anchor carrier reaches from proximally of the proximal implant part 2 to distally of the proximal implant part. It forms a seat for the proximal implant part, defines its orientation in the sleeve 28 and secures the proximal implant part against escaping to distal directions. To this end, it includes a foot piece 55 forming a proximally-facing shoulder 57 (see FIG. 9) against which the distal end of the proximal implant part 2 rests. The foot piece includes a channel 56 (see FIG. 9) for the chord, i.e. it is open towards one side to release the chord 3 when the proximal implant part is released.

Figure 9:
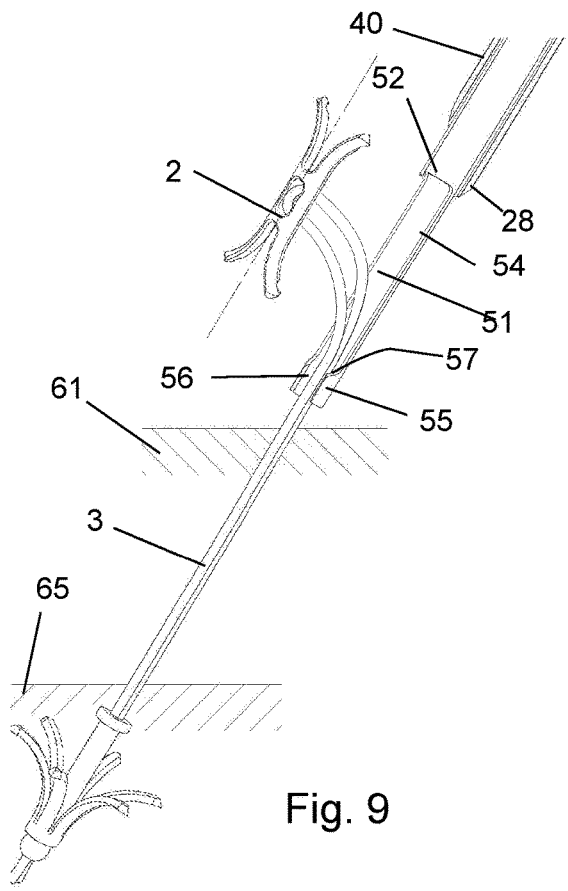

Proximally of the foot piece 55, the anchor carrier forms a shaft portion 54 (FIG. 9). The shaft portion is, in the assembled state, arranged next to the proximal implant part 2, i.e. the proximal implant part 2 and the shaft portion 54 together fit in the cross section of the sleeve 28 that fits into a cross section of the tube 40.

The tube 40 in the depicted embodiment has a distal tip 41 and is thereby shaped as a cannulated needle.

The system includes a pushing mechanism for moving the anchor carrier and the implant parts relative to the sleeve and the tube at least into distal directions (this includes the possibility of retracting the sleeve and/or the tube into a proximal direction while holding the parts still with respect to the tissue).

Such a pushing mechanism may include a pusher 52 that has some flexibility to bending movements but will be capable of transmitting axial forces. Such a pusher 52 may optionally be one-piece with the anchor carrier, i.e. the most distal portion of such a pusher may be the anchor carrier. In an example, the anchor carrier may be the appropriately shaped distal end of a flexible tube as described hereinbelow referring to FIG. 13.

The pushing mechanism may alternatively be constituted by a separate piece proximally of the anchor carrier; then optionally the anchor carrier may be fastened to the pusher so that anchor carrier may be retracted into the tube by pulling the pusher after the proximal implant part has been released.

Hereinafter, an example of the method of implanting an implant using the system is described.

For implanting in mitral valve repair surgery (generally, tricuspid valve repair surgery is carried out analogously, in the right chamber of the heart), the needle formed by the tube 40 pierces (if the tube is not piercing, then an separate means or the distal implant part may be used for piercing) the leaflet and then is advanced through the ventricle and then pierces the tissue of the papillary muscle where the distal anchor is to be anchored.

Optionally, the tube 40 may include a depth indicating marker that, depending on how surgery is carried out, may be supervised by imaging methods or by visual supervision.

In FIG. 4, the tube is illustrated to be inserted so that the distal end reaches into muscle tissue 65, especially of the papillary muscle. For implanting the distal implant portion 1, the tube is retracted while the pushing mechanism holds the implant parts and the anchor carrier still. The sleeve 28 in this protects the implant parts and the chord from being damaged by the sharp edge of the needle (FIG. 5). Then, the sleeve is also retracted until the distal implant part is released from the lumen formed by the sleeve. As soon as the distal implant part 1 is released, its legs 15 spread outwardly, thereby anchoring the distal implant part in the muscle tissue (FIG. 6).

Thereafter, the tube 40 with the sleeve 28, the anchor carrier and the proximal implant part is further retracted (FIG. 7) until the distal end of the tube 40 is proximally of the leaflet 61. Because the chord has its end attached to the distal implant part 1 and is looped through the proximal implant part 2, it will by this be pulled out of the tube 40.

Figure 10:
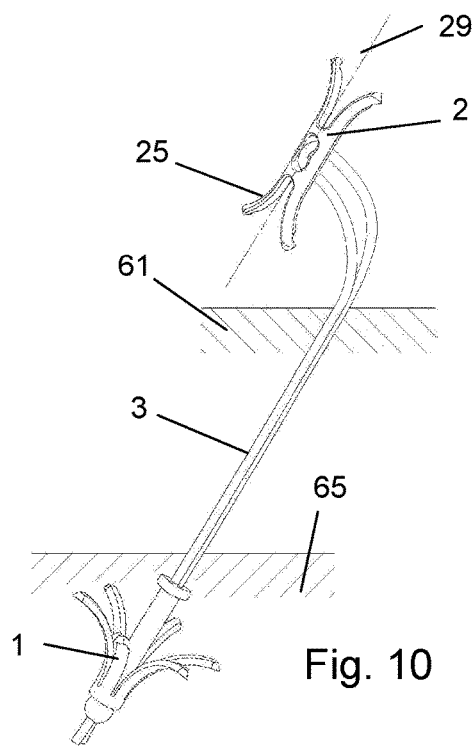
FIGS. 10 and 11 the implant during the final steps of the implantation process.
Figure 11:
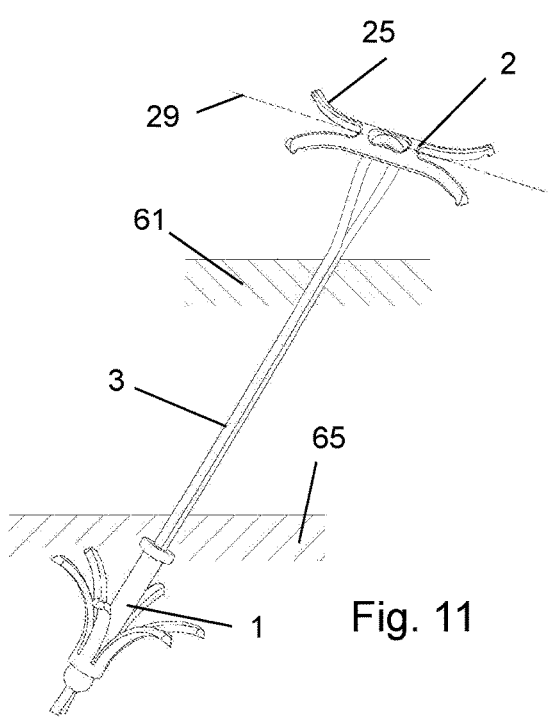

Then, again the anchor carrier with the proximal implant part and the sleeve 28 are moved forward with respect to the tube by retracting the tube while holding the anchor carrier and the sleeve 28 approximately still (FIG. 8). Thereafter, also the sleeve 28 is retracted. As soon as the proximal implant part 2 is not confined by the sleeve 28 anymore, it may fall out of the seat formed by the anchor carrier (FIG. 9). The chord 3 is prevented from being entrapped in the anchor carrier 51 by the shape of the foot piece 55 that forms a channel 56 for the chord 3. Upon release of the proximal implant part 2 from the tube, the arms 25 will spread out and form, on the lower side (that prior to the release abuts against the shaft portion 54, a spread abutment surface. Relative movements of the muscle tissue and the leaflet tissue will cause one end of the proximal anchor 2 to come into engagement with leaflet tissue, and pulling forces on the chord 3 will cause the proximal implant part 2 to tilt to align the axis 29 with the leaflet tissue (FIGS. 10 and 11). The hook features 27 (FIG. 2) will prevent the proximal implant part from shifting relative to the tissue thereafter, and after some healing time there will be ingrowth of the proximal implant part.

Figure 12:
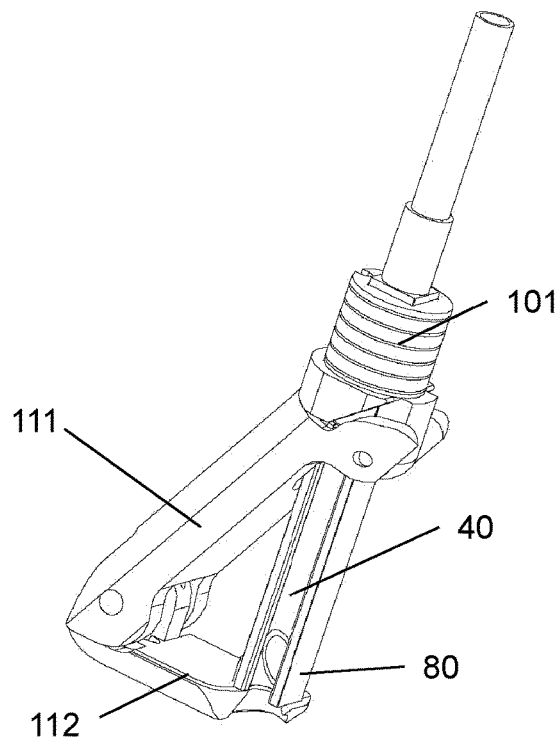
FIG. 12 a view of an auxiliary device that is used for the system and for carrying out the method if applied in minimally invasive surgery.

The method of implanting the implant, as described in detail hereinbefore, especially may include piercing the leaflet and advancing the tube through the pierced leaflet. If the implantation is carried out by a surgical operation of the open and drained heart, this may be achieved by the surgeon possibly using standard techniques. If alternatively the operation is carried out in a minimally invasive manner, the leaflet has to be held still for the operation. This may for example be done by a releasable mechanism as illustrated in FIG. 12. The illustrated mechanism comprises, attached to an outer tube a main body 101, a swing-out arm 111 with a jaw 112, and a pressing member 80 slidable with respect to the main body 101. For the operation, the leaflet is clamped between the pressing member 80 and the jaw 101. The tube 40 is slidable with respect to the pressing member, for example in a central lumen of the pressing member or in a groove defined by the pressing member. The jaw includes a recess for the tube 40. Once the leaflet is held between the jaw and the pressing member, the tube is advanced towards the distal direction, piercing the leaflet, and then moved further. The grip on the leaflet is, for example, only released after release of the proximal implant part in the process described hereinbefore.

Figure 13:
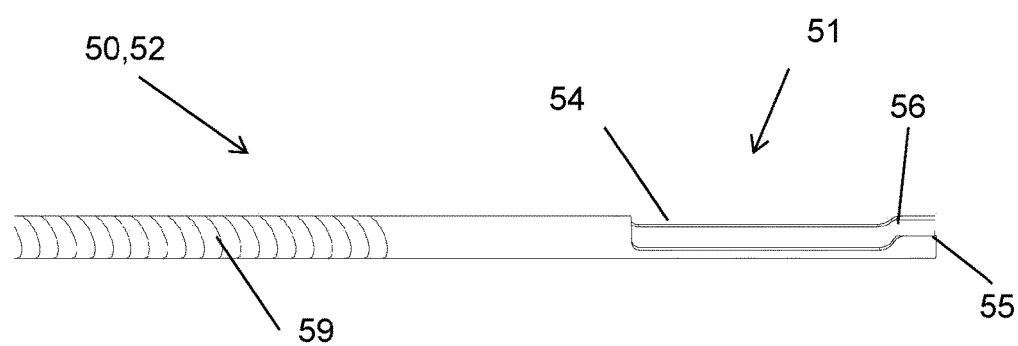
FIG. 13 a view of an embodiment of the anchor carrier.

FIG. 13 yet shows an anchor carrier 51 one-piece with a flexible pusher tube 52. A hypotube 50 with a laser-manufactured cut or laser-manufactured cuts 59, for example a helical cut, towards its distal end is provided with a clearance for the proximal implant part. The remaining portion of the tube 50, 52 forms the shaft portion 54. To form the foot piece 55, at the distal end the tube 50, 52 is left intact except for a narrow axially-running recess that serves as the channel 56.

Instead of a hypotube of the described kind, also other kinds of suitable tubular elements could be used, for example of a suitable more flexible material (metal, plastic, etc.).

What is claimed is:

1. A system for repairing an atrioventricular heart valve, the system comprising
a tubular element having an outer, distal end,
a distal implant part arranged in the tubular element,
an artificial or allograft or xenograft chord arranged in the tubular element,
a proximal implant part arranged in the tubular element, and
an anchor carrier arranged in the tubular element,
the distal implant part and the proximal implant part being arranged in the tubular element beside one another,
wherein the distal implant part is mounted to be releasable from the tubular element by at least one of: pushing the anchor carrier and the implant parts into a distal direction relative to the tubular element; retracting the tubular element into a proximal direction relative to the anchor carrier and the implant parts,
the proximal implant part being assembled with the anchor carrier inside the tubular element so that the tubular element prevents, after release of the distal implant part, the proximal implant part from escaping from the anchor carrier as long as the anchor carrier is within the tubular element, wherein the anchor carrier reaches from proximally of the proximal implant part to distally of the proximal implant part, forming a seat for the proximal implant part, defining an orientation of the proximal implant part in the tubular element and securing the proximal implant part against escaping to distal directions by comprising a foot piece distally of the proximal implant part,
whereby the proximal implant part is releasable from the tubular element by at least one of: pushing the anchor carrier with the proximal implant part into a distal direction relative to the tubular element; retracting the tubular element into a proximal direction relative to the anchor carrier with the proximal implant part,
wherein the foot piece comprises a channel for the chord that is open towards one side to release the chord when the proximal implant part is released.

2. The system according to claim 1, wherein the proximal implant part is assembled with the anchor carrier in a manner that the proximal implant part is released automatically from the anchor carrier as soon as the proximal implant part is outside of the tubular element.

3. The system according to claim 2, wherein the proximal implant part is assembled with the anchor carrier in a manner that the proximal implant part is released from the anchor carrier, as soon as the proximal implant part is outside of the tubular element, without any active mechanism that causes the release, by being moved out of the tubular element.

4. The system according to claim 1, wherein the proximal implant part escapes from the seat by being moved in a radial direction once it is released from the tubular element.

5. The system according to claim 1, wherein the anchor carrier comprises a shaft portion extending along the proximal implant part and the foot piece distally of the shaft portion, the foot piece forming a proximally-facing shoulder that secures the proximal implant part against escaping to distal directions.

6. The system according to claim 1, wherein at least the proximal implant part comprises a self-spreading portion spreading radially outside when the proximal implant part is released from the tubular element.

7. The system according to claim 1, wherein the chord connects the proximal and distal implant parts.

8. The system according to claim 1, wherein the chord is arranged proximally of the proximal implant part.

9. The system according to claim 1, wherein the chord has a fixed length and is mounted to the proximal and distal implant parts in a manner that it defines a maximum distance between the proximal and distal implant parts after implantation.

10. The system according to claim 1, wherein the chord is coupled to the proximal implant part in a manner that a pulling force on the chord does not transmit any torque on the proximal implant part lying flat on the leaflet.

11. The system according to claim 1, wherein the tubular element is a tube having a distal cutting edge and thereby serving as a cannulated needle.

12. The system according to claim 1, wherein the tubular element is a sleeve with a non-cutting distal end.

13. The system according to claim 12, further comprising a tube encompassing the sleeve, the tube having a distal cutting edge and thereby serving as a cannulated needle.

14. A method of replacing or supplementing damaged natural chordae tendineae of a human or animal heart of a patient in need thereof, the method comprising the steps of:
providing the system according to claim 1;
advancing the tubular element from an atrial side to a leaflet of an atrioventricular valve of the heart, piercing the leaflet and advancing the tubular element through the pierced leaflet and through the ventricle towards tissue;
releasing the distal implant part from the tubular element and thereby implanting it in the tissue;
retracting the tubular element and releasing the proximal implant part proximally of the leaflet, on the atrial side thereof; and
removing the tubular element,
wherein either the proximal implant part and the distal implant part are connected by the chord in the system, or the method comprises the additional step of connecting the proximal and distal implant parts by the chord.

15. The method according to claim 14, wherein releasing the proximal implant part comprises letting a self-expanding portion of the proximal implant part expand.

16. The method according to claim 14, wherein releasing the proximal implant part comprises causing the proximal implant part to lie flat on an atrial side of the leaflet.

17. The method according to claim 14, wherein releasing the proximal implant part comprises moving the tubular element relative to the anchor carrier in a proximal direction until the proximal implant part is outside of the tubular element, whereby the proximal implant part is released automatically from the anchor carrier.

* * * * *